United States Patent [19]

Miller et al.

[11] Patent Number: 5,672,968

[45] Date of Patent: Sep. 30, 1997

[54] NMR CONCRETE ANALYSIS

[75] Inventors: Melvin N. Miller, Wynnewood; Manfred G. Prammer, West Chester, both of Pa.; Moti Huber, Rehovot, Israel

[73] Assignee: Numalog, Nes Ziona, Israel

[21] Appl. No.: 650,044

[22] Filed: May 17, 1996

[30] Foreign Application Priority Data

Mar. 11, 1996 [IL] Israel .................................. 117443

[51] Int. Cl.$^6$ .................................................. G01V 3/00
[52] U.S. Cl. ............................................ 324/300; 324/306
[58] Field of Search .................................. 324/300, 304, 324/306, 307, 309, 312, 318, 322, 303

[56] References Cited

U.S. PATENT DOCUMENTS

| | | | |
|---|---|---|---|
| 4,769,601 | 9/1988 | Herrick | 324/300 |
| 5,235,276 | 8/1993 | Lew | 324/306 |
| 5,278,501 | 1/1994 | Guilfoyle | 324/306 |
| 5,519,319 | 5/1996 | Smith et al. | 324/306 |

OTHER PUBLICATIONS

A.R. Brough et al., A Study of the Pozzolanic Reaction by Solid State Si–29 NMR Using Selective Isotopic Enrichment, J. Materials Sci., 30:1671–1678.

L.J. Schreiner et al., NMR Line Shape–Spin–Lattice Relaxation Correlation Study of Portland Cement Hydration, J. Amer. Ceram. Soc., 68[1]:10–16.

R. Blinc et al., NMR Relaxation Study of Absorbed Water in Cement and Tricalcium Silicate Pastes, J. Amer. Ceram. Soc., 61[1]:35–39.

L. Barbic et al., The Determination of Surface Development in Cement Pastes by NMR, J. Amer. Ceram. Soc., 65[1] :25–30.

E. Laganas et al., Analysis of Complex H–1 NMR Relaxation Measurements in Developing Porous Structures—A Study in Hydrating Cement, J. Applied Physics, 77:3343–3348.

H.C. Gran, Fluorescent Liquid Replacement Technique, a Means of Crack Detection and Water/Binder Ratio Determination In High–Strength Concretes, Cement & Concrete Res., 25:1063–1074.

S. Kwan et al., Si–29 and Al–27 MASNMR Study of Stratlingite, J. Amer. Ceram. Soc., 78:1921–1926.

M. Bogdan et al., Single–Point Imaging of Partially Dried, Hydrated White Portland Cement, J. of Magnetic Resonance, Series A, 116:266–269.

J. Link et al., Water Transport in Concrete, Magnetic Resonance Imaging, vol. 12, No. 2, 1994, pp. 203–205.

F. Papavassillou et al., H Nuclear Magnetic Resonance Imaging of Water Diffusion in Hardened Cement Pastes, J. Am. Ceram. Soc., 76:2109–2111.

R.A. Hanna et al., Solid State Si–29 and Al–27 NMR and FTIR Study of Cement Pastes Containing Industrial Wastes and Organics, Cement & Concrete Res., 25:1435–1444.

X.D. Cong et al., Effects of the Temperature and Relative Humidity on the Structure of C–S–H Gel, Cement & Concrete Res., 25:1237–1245.

S.U. Aldulaijan et al., Si–29 MASNMR Study of Hydrated Cement Paste and Mortar Made With and Without Silica Fume, J. Amer. Ceram. Soc., 78:342–346.

*Primary Examiner*—Louis M. Arana
*Attorney, Agent, or Firm*—Ladas & Parry

[57] ABSTRACT

A method for measuring or predicting a property of a porous material while curing, the porous material including therein a liquid which undergoes metamorphosis and which is present in the porous material in different phases during curing, the method including the steps of performing a low frequency, spin-echo nuclear magnetic resonance (NMR) measurement of each phase of the liquid, and correlating the NMR measurement, or extrapolating the property, in accordance with a predetermined relationship between the property and the NMR measurement.

17 Claims, 6 Drawing Sheets

NMR CONCRETE ANALYSIS

FIELD OF THE INVENTION

The present invention relates to apparatus and methods for measuring and predicting properties of porous materials while curing.

BACKGROUND OF THE INVENTION

A. BACKGROUND OF THE PROBLEM OF CONCRETE ANALYSIS

Concrete, which is used for construction, must be analyzed to determine the structural properties, particularly strength, potential for shrinkage, and ability to accept coverings (e.g., tiles), of the final cured concrete.

Concrete is mainly a mixture of water, cement, sand, and gravel. It is known that the fraction of water in the mixture during the preparation stage, is one of the most crucial parameters responsible for the strength of the final concrete.

The water in concrete appears in three states during curing—chemically bound, capillary bound, and free water. The relative fraction of water in these three states changes during curing with some of the water evaporating away from the concrete surface.

It is known that the amount of water that ends up chemically bound is highly correlated to the compressive strength of the concrete. Further, it is known that the amount of water that is capillary bound is correlated to the remaining potential for shrinkage of the concrete. The capillary bound and free water are also correlated to the readiness of a concrete structure to accept a covering.

The traditional prior art methods for testing the strength of concrete require 28 days to complete. The builder usually does not or cannot delay construction 28 days to receive the test results. Rather, the construction usually continues in the hope that the concrete is sound. If in the final analysis, the concrete does not meet the standards, the building may have to be reinforced or even torn down, perhaps incurring major additional costs. Thus, a method for quick analysis of concrete properties which predicts its final strength or measures the structure strength in situ while curing, is very desirable.

In addition, when concrete is utilized as a strength bearing member, it would be useful to know when "shrinkage" of the concrete has been completed so as not to load the member prematurely. Potential shrinkage is known to be correlated to the volume of capillary bound water in the concrete. The premature addition of load bearing members could lead to cracking of the concrete structure.

Further, the readiness of concrete floors to accept tiles or other covering depends upon its water content and the fraction of the water that is free and capillary bound.

There currently is no direct measurement utilized in the industry of the latter two applications. Since curing depends heavily on the ingredients and environment (e.g., moisture and temperature), costly errors are often made.

Methods for determining concrete strength, potential shrinkage, and readiness to accept coverings (e.g., tiles) on concrete samples in situ using nuclear magnetic resonance (NMR) have been developed by the inventors. In order to understand the basics of these methods, a short description of NMR principles is now presented.

B. NMR TERMINOLOGY

The NMR techniques involve placing a sample in a homogeneous magnetic field which is subjected to a pulse of radio-frequency radiation. There are charged particles in the sample which undergo a Larmor precession, i.e., a common rotation superposed by the magnetic field upon the motion of the system of charged particles, all the charged particles having the same ratio of charge to mass.

The absorption of energy by the sample is almost instantaneous. However, the loss of energy, i.e., the nuclear relaxation, is a type of exponential decay process which has time constants. Relaxation occurs when stimulated by local magnetic fields having components at the Larmor frequency, i.e., the angular frequency of the Larmor precession. (The precession and frequency are named after Sir Joseph Larmor, British physicist, who died in 1942.)

There are two distinct types of nuclear relaxation: spin-lattice relaxation and spin-spin relaxation.

Spin-lattice relaxation is an energy effect, and is the loss of the excess energy resulting from the excitation pulse to the surroundings, or lattice, as thermal energy. The time constant associated with spin-lattice relaxation is called T1.

Spin-spin relaxation is an entropy effect, and is related to the loss of phase coherence induced by the excitation pulse. The time constant associated with spin-spin relaxation is called T2.

There are various imaging methods which make use of either the spin-lattice or spin-spin relaxations. One is the constant-time imaging (CTI) method, a variation of which is the single-point imaging (SPI) method. Another method is called the spin-echo method, in which the radio-frequency field is applied in a sequence of two kinds of pulses, separated by a time interval $t_e$, and a decayed sequence of echoes are observed after each pulse.

C. PRIOR ART METHODS FOR MEASURING CEMENT PROPERTIES WITH NMR

U.S. Pat. No. 4,769,601 describes a method and apparatus for determining the extent of setting of cement and its strength as it sets by means of a pulsed NMR spectrometer. T1 measurements are made while agitating the cement to simulate transportation and placement thereof.

There are articles in the scientific literature describing the use of NMR to study chemical dynamics of cement hydration. M. Bogdan et al., "Single-Point Imaging of Partially Dried, Hydrated White Portland Cement", J. of Magnetic Resonance, Series A, 116:266–269 discuss using the SPI method. The article states that "several groups have attempted to image water invasion of cured concrete samples using spin-echo imaging methods." These attempts are reported by J. Link et al., Magn. Reson. Imaging, 12:203, and F. Papavassillou et al., J. Am. Ceram. Soc., 76:2109. In regard to these attempts, Bogdan et al. state that "the spin-spin relaxation times of water in these rehydration experiments is only a few milliseconds, so the quality of traditional spin-echo images is disappointing." Bogdan et al. also state that in their study, "short echo-time, one-dimensional, spin-echo profiles of moist cured white-cement paste cylinders displayed poor signal-to-noise and geometric distortions from the ideal profile geometry."

Other scientific articles describing the use of NMR to study chemical dynamics of cement hydration, and which all do not use spin-echo methods or fail to successfully use spin-echo methods, include E. Laganas et al., "Analysis of Complex H-1 NMR Relaxation Measurements in Developing Porous Structures—A Study in Hydrating Cement", J. Applied Physics, 77:3343–3348; H. C. Gran, "Fluorescent Liquid Replacement Technique, A Means of Crack Detection and Water/Binder Ratio Determination in High-Strength Concretes", Cement & Concrete Res., 25:1063–1074; J. Kaufmann et al., "One-Dimensional Water Transport in Concrete", Materials & Structures, 28:115–124; S. Kwan et al., "Si-29 and Al-27 MASNMR Study of Stratlingite", J. Amer. Ceram. Soc., 78:1921–1926; R. A. Hanna et al., "Solid State Si-29 and Al-27 NMR and FTIR Study of Cement Pastes Containing Industrial Wastes and Organics", Cement & Concrete Res., 25:1435–1444; X. D. Cong et al., "Effects of the Temperature and Relative Humidity on the Structure of C—S—H Gel", Cement & Concrete Res., 25:1237–1245; S. U. Aldulaijan et al., "Si-29 MASNMR Study of Hydrated Cement Paste and Mortar Made With and Without Silica Fume", J. Amer. Ceram. Soc., 78:342–346; A. R. Brough et al., "A Study of the Pozzolanic Reaction by Solid State Si-29 NMR Using Selective Isotopic Enrichment", J. Materials Sci., 30:1671–1678; Y. Okada et al., "Influence of Starting Materials on the Formation of 1.1-NM-Tobermorite", J. Ceram. Soc. of Japan, 102:1148–1153; L. J. Schreiner et al., "NMR Line Shape-Spin-Lattice Relaxation Correlation Study of Portland Cement Hydration", J. Am. Ceram. Soc., 68[1]:10–16; R. Blinc et al., "NMR Relaxation Study of Adsorbed Water in Cement and Tricalcium Silicate Pastes", J. Am. Ceram. Soc., 61[1]:35–39; and L. Barbic et al., "The Determination of Surface Development in Cement Pastes by NMR", J. Am. Ceram. Soc., 65[1]:25–30.

Thus, although using T1 measurements to determine properties of concrete while curing is well known, using spin-echo methods for making T2 measurements have not been successful. As mentioned above, one of the main reasons for the lack of success in making T2 measurements is the short relaxation times. However, the very same short T2 relaxation times make it desirable to develop a method which uses T2 measurements instead of T1, because the concrete property information is obtained much quicker. The present invention provides such methods.

SUMMARY OF THE INVENTION

The present invention seeks to provide greatly improved apparatus and methods for measuring and predicting properties of porous materials while curing.

In particular, the present invention provides methods for determining concrete strength, potential shrinkage, and readiness to accept coverings (e.g., tiles) on concrete samples in situ using nuclear magnetic resonance (NMR). An analysis of concrete performed in accordance with the methods of the present invention, takes a few hours instead of the 28 days of the prior art, thus providing reliable and quick information to the builder and virtually eliminating any financial risk.

The embodiments of the present invention are described hereinbelow with reference to the curing of concrete. However, it is appreciated that the present invention is applicable not only to curing of concrete, but to any porous material which contains a liquid which undergoes metamorphosis during curing, and in which a spin-echo NMR measurement may be made of the different phases of the liquid while curing.

The present invention uses low frequency (approximately 1 MHz) NMR, which the inventors have found to provide the desired quality of spin-echo measurements.

The present invention makes use of the NMR spin-echo method to analyze the concrete. By analyzing the NMR signal from a fresh mixture of concrete by means of the T2 distribution, one can estimate properties, such as strength, potential shrinkage, or readiness to accept coverings, of the final cured concrete by measuring the metamorphosis of the water that is trapped in the concrete mixture as a function of time.

The water appears in the concrete in three different phases:
  a. Free water—T2 relaxation time of 50–200 ms.
  b. Capillary bound water—T2 relaxation time of 15–30 ms.
  c. Chemically bound water—T2 relaxation time less than 0.2 ms.

Each kind of concrete mixture has its own unique T2 distribution for each water phase, as well as a unique proportion of the quantity of water at each phase. A different behavior of the time dependent T2 distribution indicates a different final strength, or other property, of the concrete. Tables may be prepared for a specific type of concrete, correlating the T2 distribution to a concrete property, such as strength. By comparing measurements made on a new concrete sample with the known tables, one can measure or predict the strength, or other property of the new concrete sample.

As stated hereinabove, the prior art has been unsuccessful in using the spin-echo method. The present invention uses a low frequency (approximately 1 MHz), low field NMR spectrometer, such as the CoreSpec-1000, currently available from NUMALOG LTD./NUMAR CORPORATION. The CoreSpec-1000 spectrometer measures changes in the T2 distribution at two different temperatures, which can be used to determine the diffusion coefficient of the concrete mixture. The diffusion coefficient and the influence of temperature on the phase change of the water improve the accuracy of measuring and predicting concrete properties.

By using the CoreSpec-1000 spectrometer, the water measurements can be made easily, during a few hours, instead of 28 days with the present traditional measuring method, which is the only currently acceptable standard method.

Another preferred embodiment includes a probe which can make the NMR T2 distribution measurements in a sensitive volume below the surface of the concrete. An advantage of this embodiment is that the actual structure may be measured in real time, at different points of the structure, to allow the builder to monitor the quality of the concrete. This might avoid having to destroy and reconstruct the concrete structure at a later time. Measuring several points allows greater assurance of quality over the entire structure.

There is thus provided in accordance with a preferred embodiment of the present invention, a method for measuring a property of a porous material while curing, the porous material including therein a liquid which undergoes metamorphosis and which is present in the porous material in different phases during curing, the method including the steps of:
  performing a low frequency, spin-echo nuclear magnetic resonance (NMR) measurement of each phase of the liquid; and
  correlating the NMR measurement with a predetermined relationship between the property and the NMR measurement.

There is also provided in accordance with a preferred embodiment of the present invention, a method for predicting a property of a porous material while curing, the porous material including therein a liquid which undergoes metamorphosis and which is present in the porous material in different phases during curing, the method including the steps of:
  performing a low frequency, spin-echo nuclear magnetic resonance (NMR) measurement of each phase of the liquid; and extrapolating the property based on a predetermined relationship between the property and the NMR measurement.

There is further provided in accordance with a preferred embodiment of the present invention, a method for measuring a property of a structure made of concrete, the concrete including therein free water, capillary bound water and chemically bound water, the method including the steps of:

performing an in situ, low frequency, spin-echo nuclear magnetic resonance (NMR) measurement of the free water, the capillary bound water and the chemically bound water; and correlating the NMR measurement with a predetermined relationship between the property and the NMR measurement.

There is also provided in accordance with another preferred embodiment of the present invention, a method for predicting a property of a structure made of concrete, the concrete including therein free water, capillary bound water and chemically bound water, the method including the steps of:

performing an in situ, low frequency, spin-echo nuclear magnetic resonance (NMR) measurement of the free water, the capillary bound water and the chemically bound water; and extrapolating the property based on a predetermined relationship between the property and the NMR measurement.

In accordance with a preferred embodiment of the present invention, an RF shield is employed to substantially isolate the NMR measurement from environmental noise.

Preferably the low frequency is approximately 1 MHz.

The property may be for example, strength, potential shrinkage, or readiness to accept coverings.

There is also provided in accordance with a preferred embodiment of the present invention, apparatus for measuring a property of a structure made of concrete, the concrete including therein free water, capillary bound water and chemically bound water, the apparatus including:

at least one magnet for generating a magnetic field;

a radio frequency (RF) transmitter:

a butterfly-type surface coil electrically connected to the RF transmitter for generating RF signals; and an RF shield for substantially isolating the at least one magnet and the coil from environmental noise, wherein the apparatus creates a sensitive volume in the concrete structure for performing therein an in situ, low frequency, spin-echo nuclear magnetic resonance (NMR) measurement of the free water, the capillary bound water and the chemically bound water in the concrete.

BRIEF DESCRIPTION OF THE DRAWINGS

The present invention will be understood and appreciated from the following detailed description, taken in conjunction with he drawings in which.

DETAILED DESCRIPTION OF PREFERRED EMBODIMENTS

Figure 1:
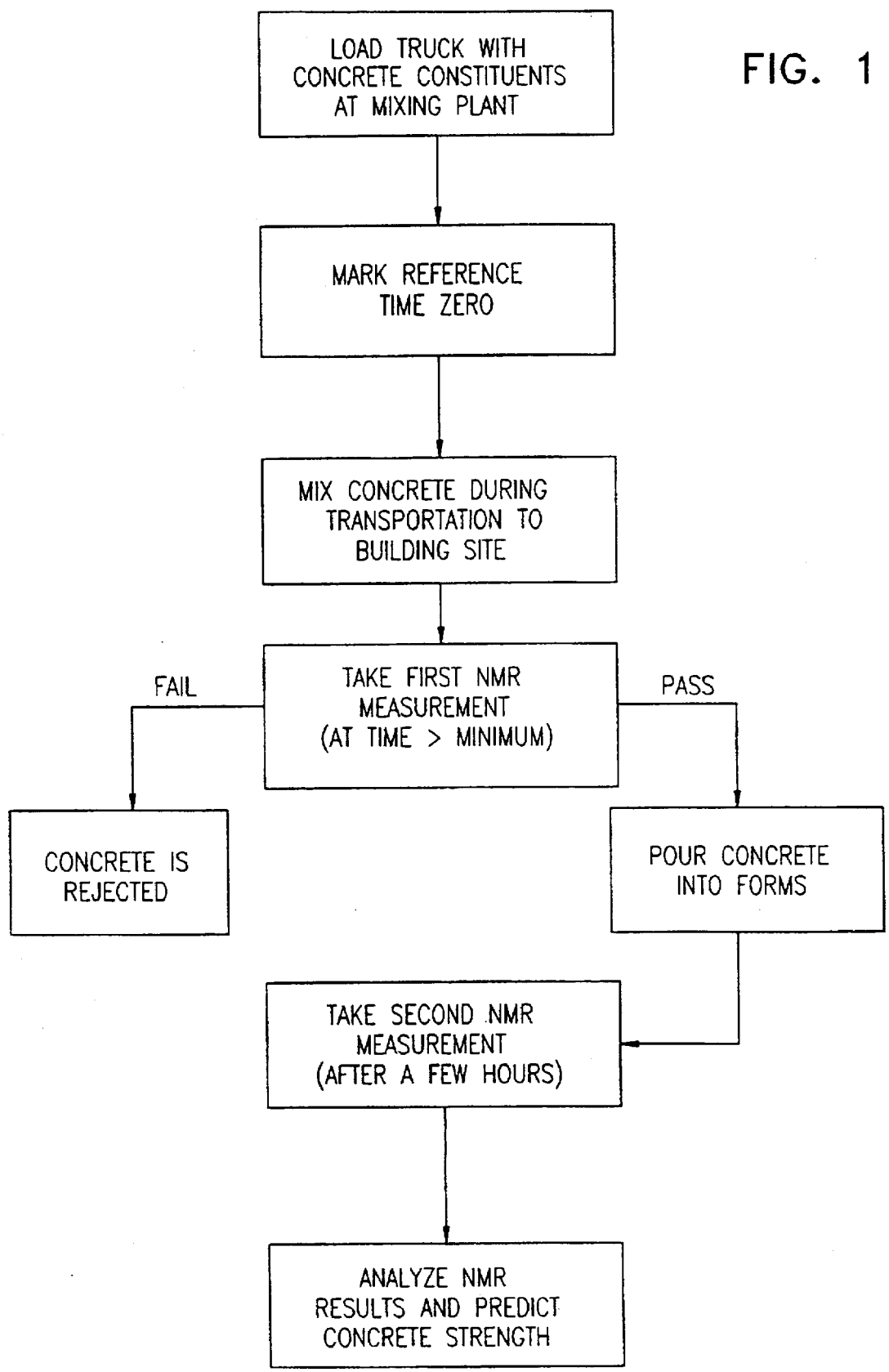
FIG. 1 is a simplified flow chart of a method for predicting a property of concrete in accordance with a preferred embodiment of the present invention.

Reference is now made to FIG. 1 which is a simplified flow chart of a method for predicting a property of concrete in accordance with a preferred embodiment of the present invention.

After loading a truck with concrete constituents at a mixing plant, the time of the concrete mixing is registered and is defined as a reference time zero. The temperature and humidity of the ambient air are recorded are used to determine the vaporization conditions of the water. Afterwards, the concrete is mixed during transportation to a building site where a first spin-echo NMR measurement of the concrete is made. A concrete property, such as strength, potential shrinkage, or readiness to accept coverings, is then determined by correlating the NMR measurement with a predetermined relationship between the property and the NMR measurement.

If the property determined by the NMR measurement does not comply with a predetermined standard, then the concrete is rejected. If the property does comply with the standard, then it may be poured to form a structure. A second spin-echo NMR measurement is then taken a few hours later. In accordance with a preferred embodiment of the present invention, a property of concrete, such as strength, potential shrinkage, or readiness to accept coverings, is then extrapolated based on a predetermined relationship between the property and the NMR measurement.

The spin-echo NMR method makes use of water found in the concrete. Water appears in concrete in three different phases: free water, capillary bound water and chemically bound water. There is a transition of free water into capillary bound water and then to chemically bound water. The T2 relaxation time is different for free water, capillary bound water and chemically bound water, as follows:

a. Free water—50–200 ms.

b. Capillary bound water—15–30 ms.

c. Chemically bound water—less than 0.2 ms.

Each kind of concrete mixture has its own unique T2 distribution for each water phase, as well as a unique proportion of the quantity of water at each phase. A different behavior of the time dependent T2 distribution leads to a different final strength, or other property, of the concrete. Tables may be prepared for a specific type of concrete, correlating the T2 distribution to a concrete property, such as strength. By comparing measurements made on a new concrete sample with the known tables, one can measure or predict the strength, or other property of the new concrete sample. Examples of changes in the water phase are shown hereinbelow in FIGS. 2–4.

The present invention uses a low frequency (approximately 1 MHz), low field NMR spectrometer, such as the CoreSpec-1000, currently available from NUMALOG LTD./NUMAR CORPORATION. The CoreSpec-1000 spectrometer has a feature which measures changes in the T2 distribution at two different temperatures, which can be used to determine the diffusion coefficient of the concrete mixture. The diffusion coefficient and the influence of temperature on the phase change of the water improve the accuracy of measuring and predicting concrete properties.

By using the CoreSpec-1000 spectrometer, the water measurements can be made easily, during a few hours, instead of 28 days with the present traditional measuring method, which is the only currently acceptable standard method.

Figure 2:
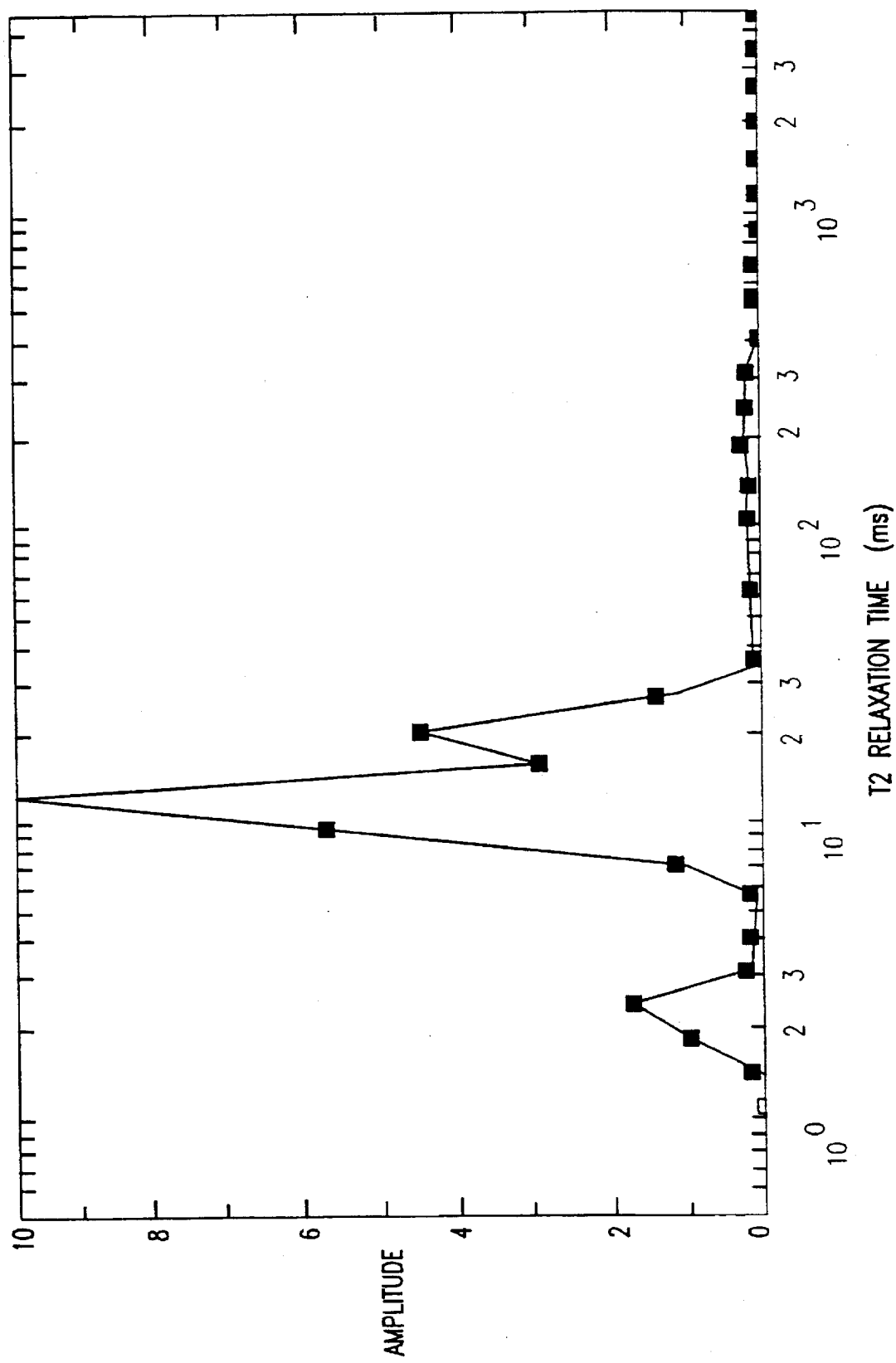
FIGS. 2 and 3 are spectral curve graphs of the T2 relaxation time of a concrete measured in accordance with a preferred embodiment of the present invention.
Figure 3:
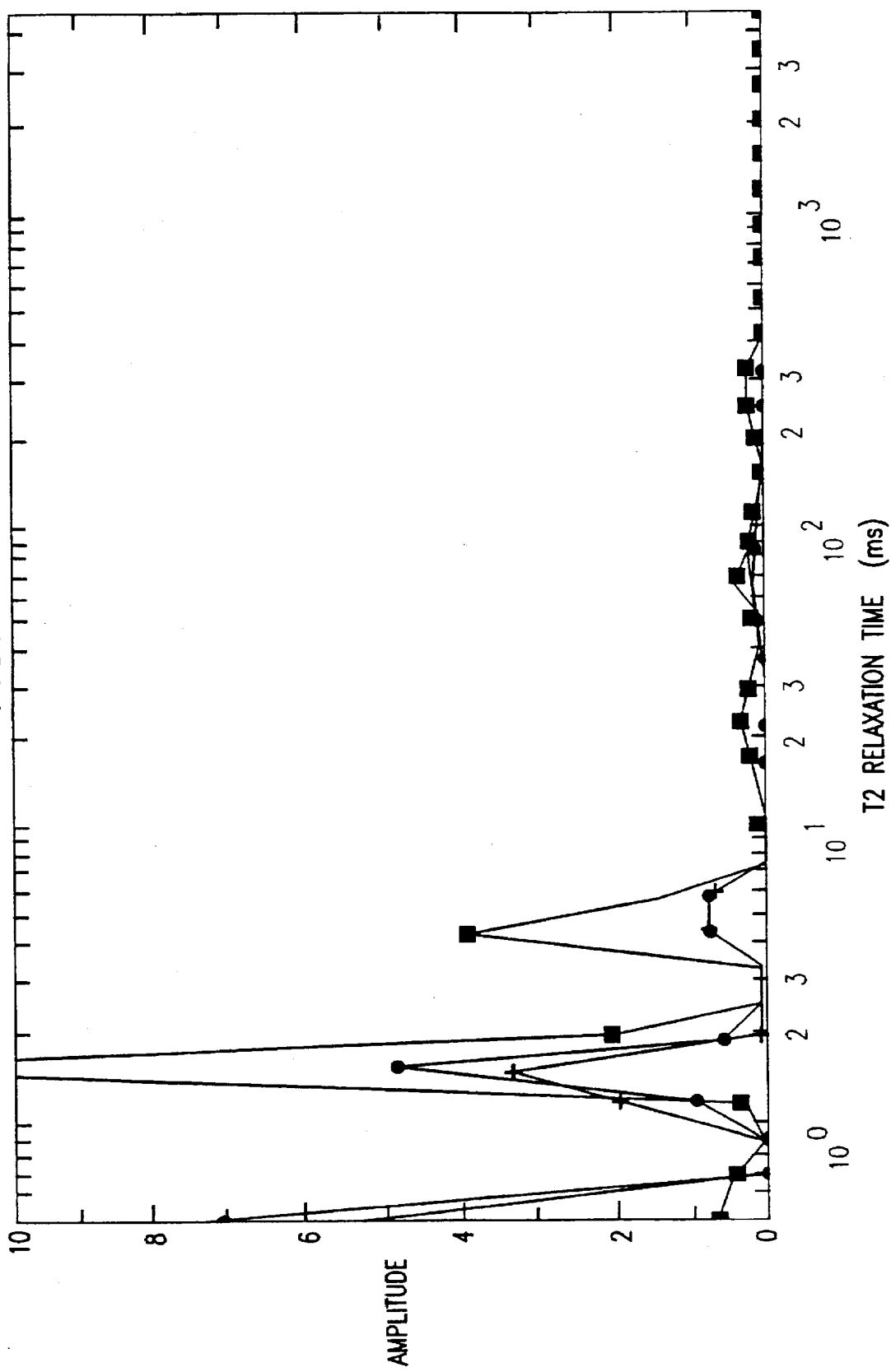

Reference is now made to FIGS. 2 and 3 which are spectral curve graphs of the T2 relaxation time of a concrete measured in accordance with a preferred embodiment of the present invention. The square, round and plus-sign points on the graphs represent measurements 24, 144 and 244 hours, respectively, after the first spin-echo measurement. The amplitude is in porosity units.

Figure 4:
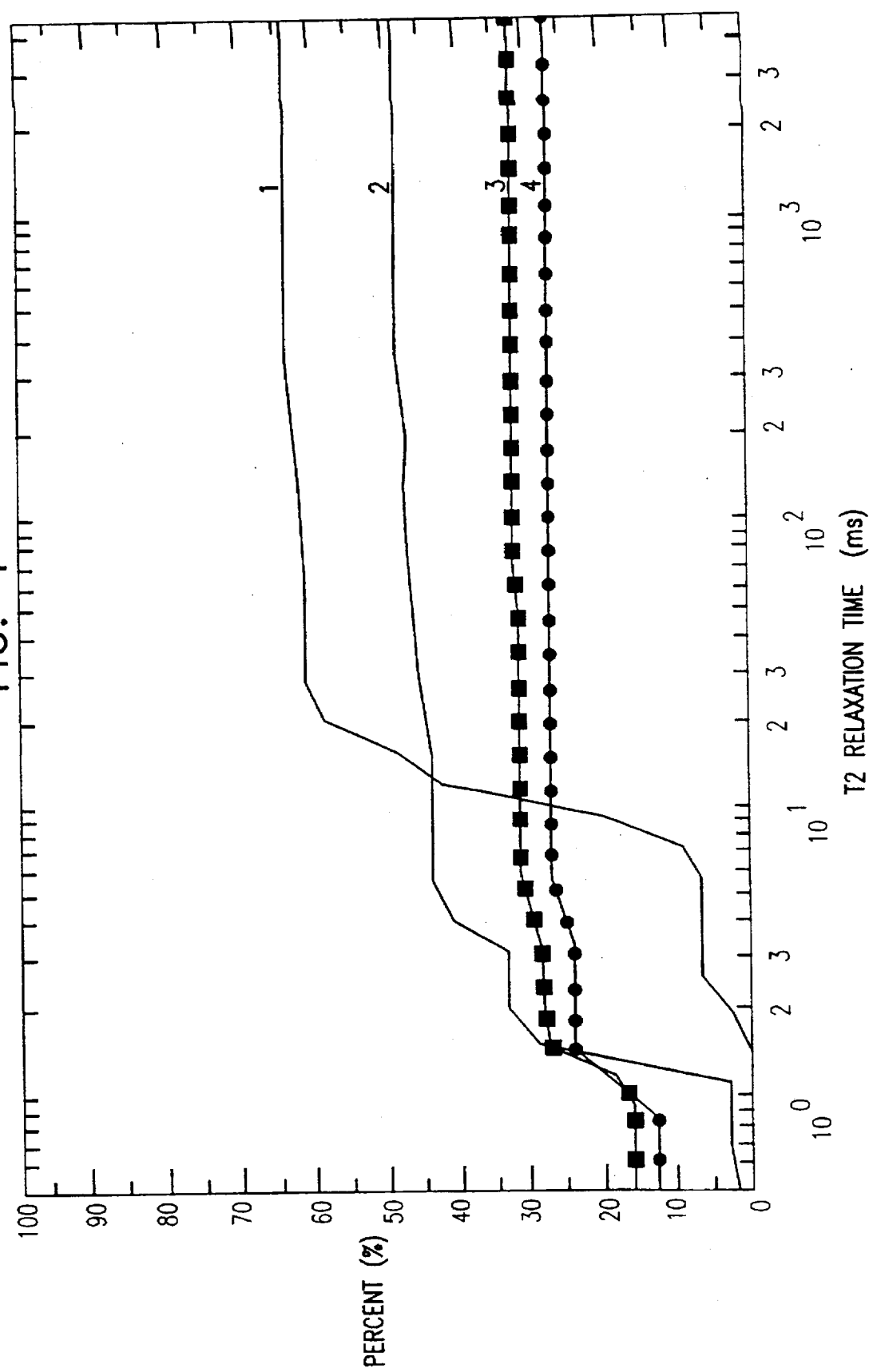
FIG. 4 is a cumulative curve graph of the T2 relaxation time of a concrete measured in accordance with a preferred embodiment of the present invention.

Reference is now made to FIG. 4 which is a cumulative curve graph of the T2 relaxation time of a concrete measured in accordance with a preferred embodiment of the present invention. Graphs 1, 2, 3 and 4 represent measurements made 0, 24, 144 and 288 hours, respectively, after the first spin-echo measurement. The percentage shown in the graph is a ratio of the sample measured as compared with a sample containing 100% water.

Figure 5:
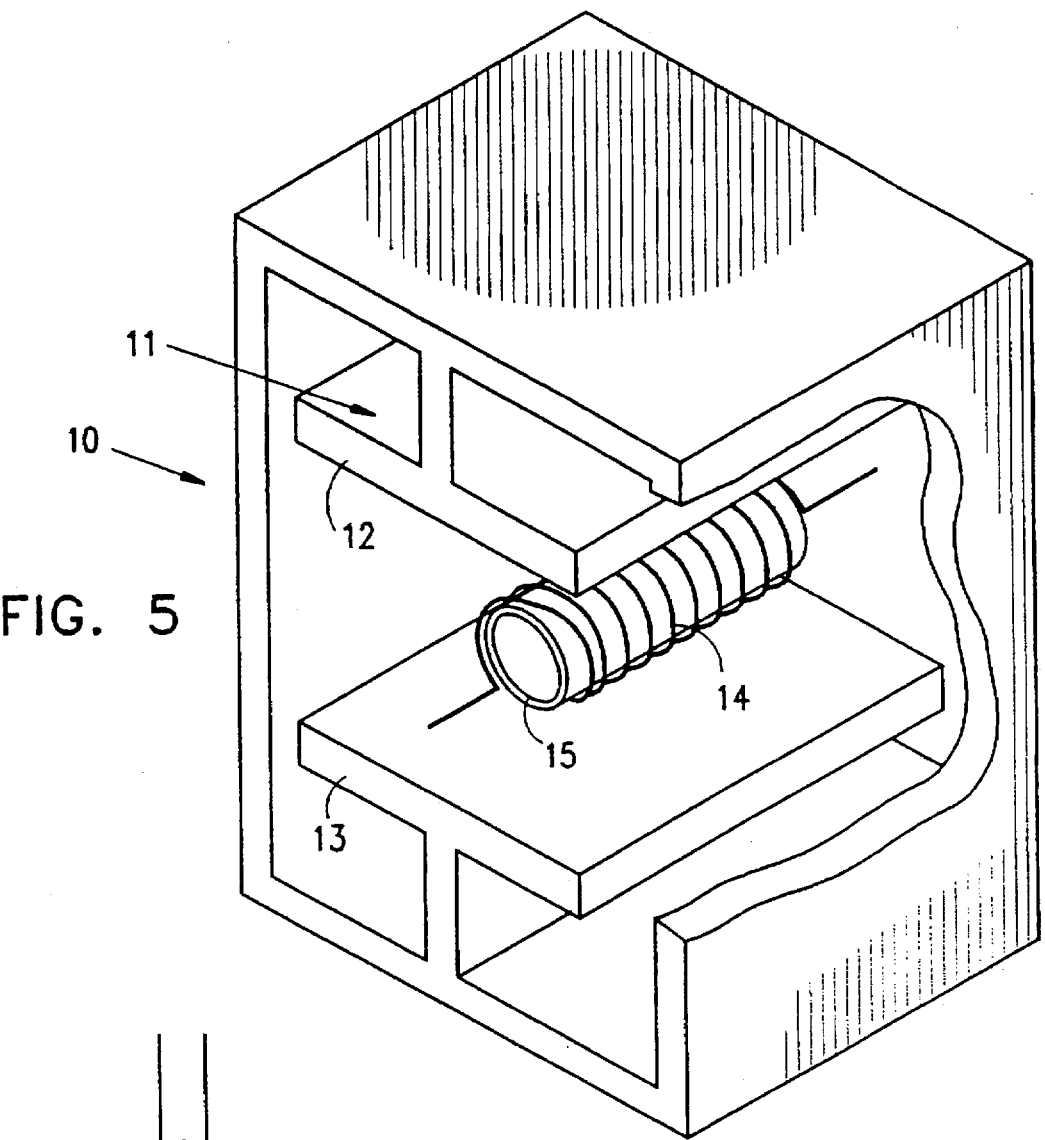
FIG. 5 is a simplified pictorial illustration of a spectrometer which may be used to measure or predict a property of concrete in accordance with a preferred embodiment of the present invention.

Reference is now made to FIG. 5 which is a simplified illustration of a spectrometer 10, which may be used to measure or predict a property of a sample of a porous material, in accordance with a preferred embodiment of the present invention.

Spectrometer 10 is preferably of the same type as the CoreSpec-1000, currently available from NUMALOG LTD./NUMAR CORPORATION. Spectrometer 10 includes a magnet 11 which has a south pole 12 and a north pole 13. An RF coil 14 is disposed intermediate south pole 12 and north pole 13. A concrete sample may be placed in a container 15, which is located in RF coil 14. Spectrometer 10 may be used to measure the T2 distribution of the sample, as described hereinabove with reference to FIG. 1.

Figure 6:
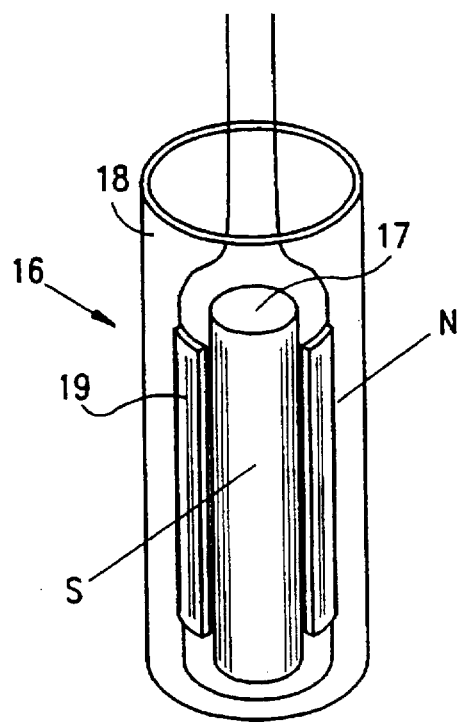
FIG. 6 is a simplified pictorial illustration of a probe which may be used to measure or predict a property of concrete in accordance with a preferred embodiment of the present invention.

Reference is now made to FIG. 6 which is a simplified illustration of a probe 16, which may be inserted in a porous material in order to measure or predict a property of the material, in accordance with a preferred embodiment of the present invention.

Probe 16 is preferably of the same type used in the MRIL system of NUMALOG LTD./NUMAR CORPORATION. Probe 16 includes a magnet 17 disposed in an insulating housing 18. The north and south poles of magnet 17 are indicated by the letters N and S in FIG. 6. A two-piece RF antenna 19 surrounds magnet 17. Probe 16 may be inserted in a concrete sample to measure the T2 distribution of a sample, as described hereinabove with reference to FIG. 1.

Figure 7A:
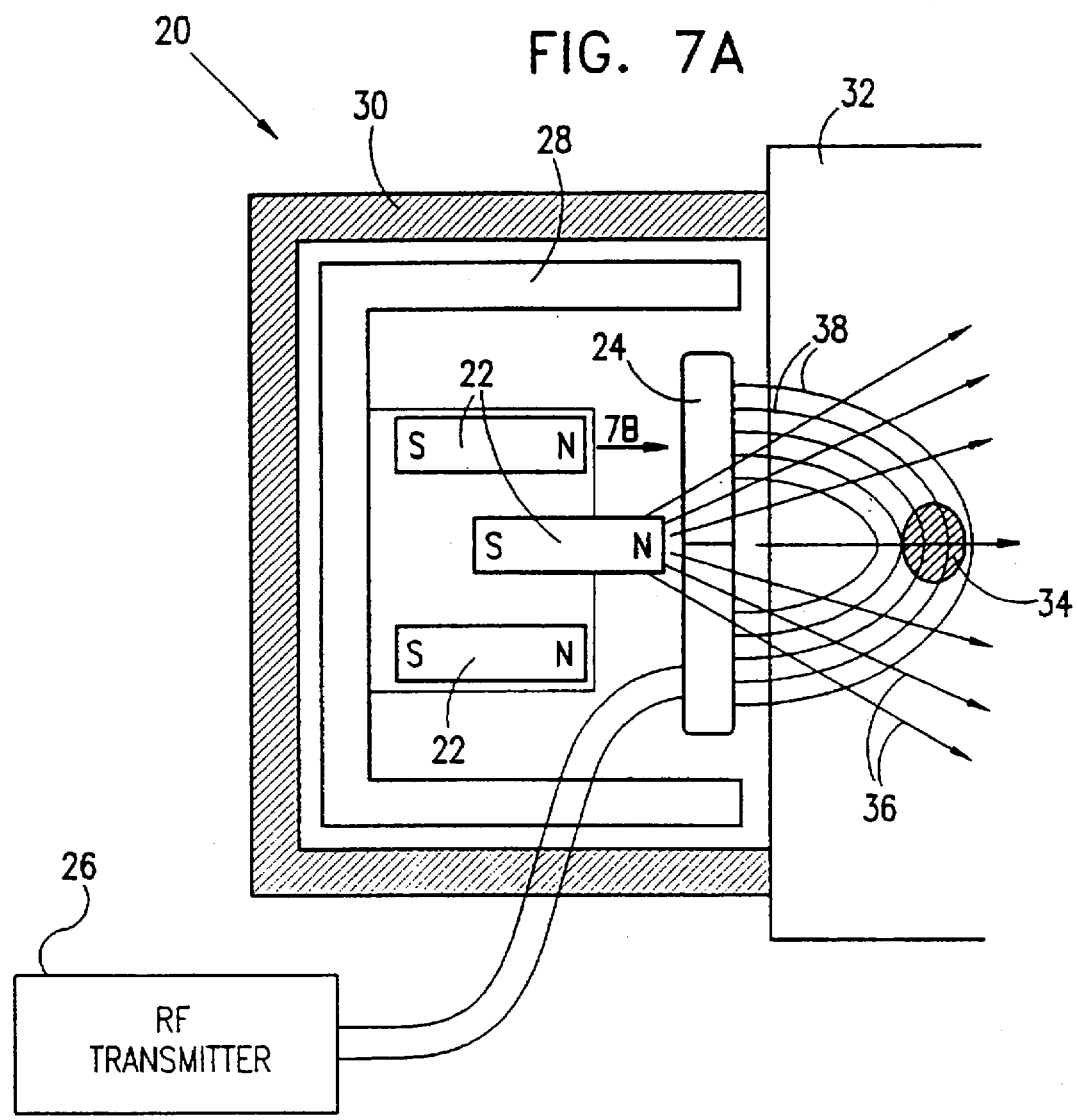
FIG. 7A is a simplified illustration of apparatus for measuring a property of concrete in a built structure, constructed and operative in accordance with a preferred embodiment of the present invention.

Reference is now made to FIG. 7A which is a simplified illustration of apparatus 20 for measuring a property of concrete in a built structure, constructed and operative in accordance with a preferred embodiment of the present invention.

Figure 7B:
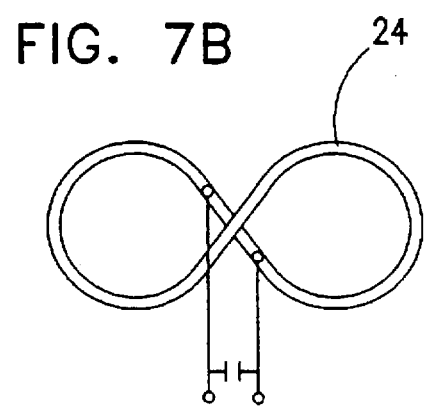
FIG. 7B is a simplified front view illustration of a butterfly-type surface coil used in apparatus of FIG. 7A, as viewed along arrow 7B in FIG. 7A.

Apparatus 20 preferably includes, inter alia, at least one, and preferably three, permanent magnets 22 for generating a magnetic field, and a butterfly-type surface coil 24. Coil 24, which is also shown in a front view illustration in FIG. 7B, is electrically connected to a radio frequency transmitter 26 for generating RF signals. Magnets 22 are preferably attached to a yoke 28. Apparatus 20 is preferably provided with an RF shield 30 for isolating the magnets 22 and coil 24 from environmental noise.

In FIG. 7A, apparatus 20 is shown placed in juxtaposition with a concrete structure 32. Magnets 22 and butterfly coil 24, energized by transmitter 26, create a sensitive volume 34 in concrete structure 32. Sensitive volume 34 is located in a region of permanent magnet field lines 36 and RF field lines 38, as is known in the art. Changes in the T2 distribution in sensitive volume 34 may be monitored as described hereinabove with reference to FIG. 1 for measuring or predicting a property of concrete in structure 30.

It will be appreciated by persons skilled in the art that the present invention is not limited to what has been particularly shown and described hereinabove. Rather, the scope of the present invention is defined only by the claims that follow:

We claim:

1. A method for measuring a property of a porous material while curing, said porous material including therein a liquid which undergoes metamorphosis and which is present in said porous material in different phases during curing, said method comprising the steps of:

performing a low frequency, spin-echo nuclear magnetic resonance (NMR) measurement of each phase of said liquid; and correlating said NMR measurement with a predetermined relationship between said property and said NMR measurement.

2. A method according to claim 1 wherein an RF shield is employed to substantially isolate said NMR measurement from environmental noise.

3. A method according to claim 1 wherein said low frequency is approximately 1 MHz.

4. A method according to claim 1 wherein said property is at least one of the following properties: strength, potential shrinkage and readiness to accept coverings.

5. A method for predicting a property of a porous material while curing, said porous material including therein a liquid which undergoes metamorphosis and which is present in said porous material in different phases during curing, said method comprising the steps of:

performing a low frequency, spin-echo nuclear magnetic resonance (NMR) measurement of each phase of said liquid; and extrapolating said property based on a predetermined relationship between said property and said NMR measurement.

6. A method according to claim 5 wherein an RF shield is employed to substantially isolate said NMR measurement from environmental noise.

7. A method according to claim 5 wherein said low frequency is approximately 1 MHz.

8. A method according to claim 5 wherein said property is at least one of the following properties: strength, potential shrinkage and readiness to accept coverings.

9. A method for measuring a property of a structure made of concrete, the concrete including therein free water, capillary bound water and chemically bound water, said method comprising the steps of:

performing an in situ, low frequency, spin-echo nuclear magnetic resonance (NMR) measurement of said free water, said capillary bound water and said chemically bound water; and correlating said NMR measurement with a predetermined relationship between said property and said NMR measurement.

10. A method according to claim 9 wherein an RF shield is employed to substantially isolate said NMR measurement from environmental noise.

11. A method according to claim 9 wherein said low frequency is approximately 1 MHz.

12. A method according to claim 9 wherein said property is at least one of the following properties: strength, potential shrinkage and readiness to accept coverings.

13. A method for predicting a property of a structure made of concrete, the concrete including therein free water, capillary bound water and chemically bound water, said method comprising the steps of:

performing an in situ, low frequency, spin-echo nuclear magnetic resonance (NMR) measurement of said free water, said capillary bound water and said chemically bound water; and extrapolating said property based on a predetermined relationship between said property and said NMR measurement.

14. A method according to claim 13 wherein an RF shield is employed to substantially isolate said NMR measurement from environmental noise.

15. A method according to claim 13 wherein said low frequency is approximately 1 MHz.

16. A method according to claim 13 wherein said property is at least one of the following properties: strength, potential shrinkage and readiness to accept coverings.

17. Apparatus for measuring a property of a structure made of concrete, the concrete including therein free water, capillary bound water and chemically bound water, said apparatus comprising:

at least one magnet for generating a magnetic field;

a radio frequency (RF) transmitter:

a butterfly-type surface coil electrically connected to said RF transmitter for generating RF signals; and an RF shield for substantially isolating said at least one magnet and said coil from environmental noise, wherein said apparatus creates a sensitive volume in said concrete structure for performing therein an in situ, low frequency, spin-echo nuclear magnetic resonance (NMR) measurement of said free water, said capillary bound water and said chemically bound water in said concrete.

* * * * *